US012611097B2

(12) United States Patent
Poulsen et al.

(10) Patent No.: US 12,611,097 B2
(45) Date of Patent: Apr. 28, 2026

(54) SURGICAL CAMERA FOR LAPAROSCOPIC SURGERY

(71) Applicant: ORVUE SURGICAL A/S, Nærum (DK)

(72) Inventors: Henrik Bisgaard Poulsen, Slangerup (DK); Peter Ladegaard Larsen, Copenhagen (DK)

(73) Assignee: ORVUE SURGICAL A/S, Nærum (DK)

( * ) Notice: Subject to any disclaimer, the term of this patent is extended or adjusted under 35 U.S.C. 154(b) by 410 days.

(21) Appl. No.: 18/020,850

(22) PCT Filed: Aug. 12, 2021

(86) PCT No.: PCT/EP2021/072525
§ 371 (c)(1),
(2) Date: Feb. 10, 2023

(87) PCT Pub. No.: WO2022/034183
PCT Pub. Date: Feb. 17, 2022

(65) Prior Publication Data
US 2023/0301504 A1      Sep. 28, 2023

(30) Foreign Application Priority Data
Aug. 12, 2020    (EP) .................................... 20190660

(51) Int. Cl.
*A61B 1/313*          (2006.01)
*A61B 1/00*           (2006.01)
*A61B 1/05*           (2006.01)

(52) U.S. Cl.
CPC ........ *A61B 1/3132* (2013.01); *A61B 1/00006* (2013.01); *A61B 1/00009* (2013.01); *A61B 1/00183* (2013.01); *A61B 1/053* (2013.01)

(58) Field of Classification Search
USPC .................................................. 600/136, 137
See application file for complete search history.

(56) References Cited

U.S. PATENT DOCUMENTS 5,159,446  A  *  10/1992  Hibino ............... A61B 1/00042
                                                        600/152
5,617,762  A  *   4/1997  Kirsch ................... F16M 11/10
                                                        248/661
(Continued)

FOREIGN PATENT DOCUMENTS

DE        102013211698  A1    12/2014
EP          1989990  A1    11/2008
(Continued)

OTHER PUBLICATIONS

English translation of the foreign document is provided. DE102013211698A1: 49 pages, Dec. 24, 2014.
(Continued)

*Primary Examiner* — John P Leubecker
(74) *Attorney, Agent, or Firm* — MUNCY, GEISSLER, OLDS & LOWE, P.C.

(57) ABSTRACT

A surgical camera comprising a base, an image capturing element defining a field of view and configured to exchange image data with a monitor, a connector extending between the image capturing element and the base, and a manipulator configured for movement of the image capturing element relative to the base. To facilitate free hands of the surgeon, the surgical camera forms a contact surface which can be attached to an outer skin surface of the patient and thereby fix the camera to the patient.

17 Claims, 9 Drawing Sheets

(56) References Cited

U.S. PATENT DOCUMENTS

| | | | | |
|---|---|---|---|---|
| 5,762,603 | A * | 6/1998 | Thompson | A61B 1/05 |
| | | | | 600/137 |
| 5,820,545 | A * | 10/1998 | Arbter | A61B 1/313 |
| | | | | 600/102 |
| 5,935,057 | A * | 8/1999 | Lichtman | A61B 1/0052 |
| | | | | 600/137 |
| 6,007,484 | A * | 12/1999 | Thompson | A61B 1/045 |
| | | | | 600/122 |
| 6,398,725 | B1 * | 6/2002 | Thompson | A61B 1/00096 |
| | | | | 600/137 |
| 6,695,774 | B2 * | 2/2004 | Hale | A61B 1/00179 |
| | | | | 356/241.3 |
| 6,726,675 | B1 * | 4/2004 | Beyar | A61M 25/0105 |
| | | | | 600/137 |
| 7,553,277 | B2 * | 6/2009 | Hoefig | A61B 1/00183 |
| | | | | 600/152 |
| 7,896,803 | B2 * | 3/2011 | Schara | A61B 1/00177 |
| | | | | 600/137 |
| 8,647,262 | B2 * | 2/2014 | Seifert | A61B 1/0004 |
| | | | | 600/137 |
| 2004/0243167 | A1 * | 12/2004 | Tanaka | A61B 17/00008 |
| | | | | 606/190 |
| 2006/0167342 | A1 * | 7/2006 | Bob | A61B 1/0053 |
| | | | | 600/137 |
| 2007/0055103 | A1 * | 3/2007 | Hoefig | A61B 1/00179 |
| | | | | 600/137 |
| 2008/0009675 | A1 * | 1/2008 | Kura | A61B 1/005 |
| | | | | 600/128 |
| 2008/0091066 | A1 * | 4/2008 | Sholev | A61B 90/50 |
| | | | | 600/112 |
| 2008/0255420 | A1 * | 10/2008 | Lee | A61B 17/2909 |
| | | | | 600/137 |
| 2010/0081875 | A1 | 4/2010 | Fowler et al. | |
| 2010/0160813 | A1 * | 6/2010 | Ohno | A61B 1/00105 |
| | | | | 600/562 |
| 2011/0237881 | A1 * | 9/2011 | Kunz | A61B 1/3132 |
| | | | | 600/106 |
| 2012/0130161 | A1 * | 5/2012 | Lauryssen | A61F 2/4611 |
| | | | | 600/104 |
| 2013/0245370 | A1 * | 9/2013 | Barwinkel | A61B 34/30 |
| | | | | 600/104 |
| 2014/0357952 | A1 * | 12/2014 | Krohn | A61B 1/00006 |
| | | | | 600/112 |
| 2017/0135557 | A1 * | 5/2017 | Inoue | A61B 1/051 |
| 2017/0367782 | A1 * | 12/2017 | Schuh | A61B 1/0016 |
| 2018/0140168 | A1 * | 5/2018 | Haraguchi | A61B 34/37 |
| 2018/0289391 | A1 | 10/2018 | Fuji et al. | |
| 2019/0091459 | A1 * | 3/2019 | Donaldson | A61B 17/3423 |
| 2019/0328217 | A1 | 10/2019 | Moreau et al. | |
| 2019/0388163 | A1 * | 12/2019 | Kim | G02B 23/2476 |
| 2020/0008649 | A1 * | 1/2020 | Kokubo | G02B 23/24 |
| 2020/0069386 | A1 * | 3/2020 | Betsugi | A61B 1/00045 |

FOREIGN PATENT DOCUMENTS

| | | | |
|---|---|---|---|
| EP | 2502553 | A1 | 9/2012 |
| EP | 3235417 | A1 | 10/2017 |
| WO | WO9711634 | A1 | 4/1997 |
| WO | WO2009/045827 | A2 | 4/2009 |
| WO | WO2009/045827 | A3 | 4/2009 |

OTHER PUBLICATIONS

EP search report in application No. 25203881.5 dated Jan. 22, 2026, pp. 1-9.

* cited by examiner

30

2

81

4

3

141

142

133

132

131

SURGICAL CAMERA FOR LAPAROSCOPIC SURGERY

INTRODUCTION

The present disclosure relates to a surgical camera, particularly useful for minimally invasive surgery such as laparoscopy.

BACKGROUND

Minimally invasive surgery, sometimes referred to as laparoscopic surgery or keyhole surgery, is a surgical technique where internal body parts are accessed via small incisions and typically with the support of a camera. The small incisions compared to traditional open surgery reduce haemorrhaging and shortens recovery time.

Laparoscopic surgery includes operations within the abdominal or pelvic cavities, whereas keyhole surgery performed on the thoracic or chest cavity is called thoraco-scopic surgery. Specific surgical instruments used in minimally invasive surgery include obstetrical forceps, scissors, probes, dissectors, hooks, and retractors. In recent years, electronic tools have been developed to aid surgeons further. Such electronic tools include electronic cameras, electrosurgical cutters, snares, and forceps etc., and even tools for robotic surgery, the latter allowing remote operated machines to carry out surgery at a distance from the surgeon.

SUMMARY

It is an object of embodiments of the disclosure to facilitate minimally invasive surgery and particularly to increase safety, and to provide better working conditions for the surgeon.

According to this and other objects, embodiments of the disclosure in a first aspect provide a surgical camera comprising a base, an image capturing element defining a field of view and configured to provide image data which can be visualized on an external monitor. The surgical camera further comprises a connector extending between the image capturing element and the base, and a manipulator configured for movement of the image capturing element relative to the base.

To enable hands-free or unattended use of the camera and thereby to release hands of the surgeon or assistant for other purpose, the base forms a contact surface configured to be attached to an outer skin surface of a patient. In this embodiment, the connector may extend outwards from the contact surface, or from a location close to the contact surface.

The base may therefore be attached at a location of a patient opening and the connector may be placed through the opening to position the image capturing element in a connector cavity.

The base may particularly form a soft pliable element which can take the shape of the outer skin surface of the patient. In one embodiment, the base forms a soft, pliable patch such as a soft plaster. The base may particularly be configured for sealing of the patient opening on which it is applied to thereby facilitate insufflation of the body cavity in which the image capturing element is located. For that purpose, the base may form a ring-shaped body of an adhesive extending about the connector.

The image capturing element may e.g. be placed in the peritoneal cavity, particularly after insufflation of the peritoneal cavity.

The procedure may comprise providing at least a first patient opening and a second patient opening, e.g. openings into the peritoneal cavity etc. This procedure may be performed with an obturator or surgical tools offering the same ability to penetrate skin. Such an obturator may be integrated in the surgical camera, or the surgical camera may form an obturator conduit for insertion of an obturator through the surgical camera or a part thereof. The obturator conduit may include a valve, e.g. a duckbill valve, allowing the obturator to be removed from the obturator conduit while leaving the obturator conduit leakproof.

A surgical camera of the kind described herein is attached to the outer skin surface of the patient at a location of a patient opening, or at a location where the patient opening is desired. In this position, the connector and image capturing element are placed through the patient opening. Particularly, the contact surface may be adhesively attached to the outer skin surface. Alternatively, it could be stitched to the skin surface, or it could be mechanically interlocked with the patient opening, e.g. by use of an inflatable balloon which is inflated in the patient opening or by use of a resilient lip-edge which can be elastically deformed and deflect into contact with the patient opening and thereby fix the surgical camera to the patient.

The base may comprise an insertion tube extending outwards from the contact surface and forming a connector passage for receiving the connector through the insertion tube. The insertion tube may be more rigid than the connector and thereby facilitate easier insertion of the connector through the body opening. Additionally, the connector passage may be used for holding an obturator which can pierce the skin initially, e.g. before the base is attached to the skin. The connector passage thereby forms said obturator conduit.

To facilitate liquid and gas tightness e.g. during exchange between an obturator and the connector in the connector passage and thereby facilitate a constantly inflated body cavity, the base may comprise a duckbill valve arrange to seal the connector passage.

The manipulator may be configured for movement of the image capturing element relative to the base by rotation and/or deformation of the connector.

The manipulator may be encapsulated in a housing, and the housing may be attached to the base by a structure allowing detachment and reattachment such that it is detachably attachable to the base. Particularly the housing may be outside the body cavity during use—i.e. the housing and the image capturing element is on opposite sides of the contact surface.

The connector may form part of an inner assembly located in the housing and it may extend outwards from the housing through the base, e.g. through said connector passage in the optional insertion tube of the base.

The inner assembly may be rotatable around a central axis relative to the housing via a first rotational joint. The central axis may particularly form an angle of 60-90 degrees to the contact surface.

In one embodiment, the inner assembly comprises two rotational joints, a first one of the two joints allowing rotation of the inner assembly relative to the housing and base, and a second one of the rotational joints being an internal rotational joint of the inner assembly.

The duckbill valve may be in level with the first rotational joint. This may facilitate that the duckbill can absorb forces from the joint when the inner assembly is rotated.

The manipulator may comprise a tilt-actuating rotor-ring rotatably attached to the inner assembly via the second rotational joint. The manipulator may further comprise a tilt actuating wire structure with at least one wire, and preferably at least two wires, extending from a fixation point in the connector to a point on the tilt actuating rotor-ring. This structure may allow bending of the connector by rotation of the tilt-actuating rotor-ring to thereby pull the wire relative to the connector.

The at least one wire may be arranged for movement of the image capturing element relative to the base by bending of a bendable portion of the connector, and the tilt-actuating rotor-ring may be rotatable around the central axis. The bending will be described further relative to the drawings.

Due to the two rotational joints, the inner assembly, and thus the connector can be rotated relative to the base and thus relative to the patient to which the base is attached, and the connector can be bend.

A first motor may be arranged for rotation of the inner assembly relative to the housing and a second motor may be arranged for rotation of the tilt actuating rotor-ring relative to the inner assembly and thereby for bending the connector. The first motor and the second motor each has a rotor axis, and the rotor axes are arranged with the same distance to the central axis on opposite sides of the central axis.

The first motor may engage a first inner toothing of the fixed outer shell by a first tooth wheel, and the second motor may engage a second inner toothing of the tilt actuating rotor-ring by a second tooth wheel. The first and second tooth wheels may be on opposite sides of the motors which are located adjacently on opposite sides of the central axis. In this way the first and second tooth wheels are offset in the direction of the central axis.

The first and second motor could be identical motors arranged with the rotor axes in opposite directions with respect to the central axis.

The image capturing element is activated and data communication is established between the image capturing element and the monitor. The monitor may particularly be an external monitor, and the images captured by the surgical camera can now be used by the surgeon for minimally invasive surgery and particularly for use of other surgical tools e.g. inserted through a second patient opening or through further patient openings. Alternatively, or additionally, a monitor may be attached directly to the base or to the housing which houses inter alia the inner assembly which constitutes a part of the manipulator.

If the contract surface is attached to the outer skin surface, the camera follows any movement of the skin or patient body and pains or discomfort arising from relative movement between the camera and the patient can be minimized.

The image capturing element may comprise a camera element such as a CCD (charge coupled diode), e.g. in combination with a light source.

In one embodiment, the image capturing element comprises a light conductive fibre optic extending through the connector and having a free image capturing tip. At an opposite end of the fibre optic, the image could be converted to an electrical signal, e.g. by a CCD etc. In this embodiment, the CCD could be located in the housing.

The image capturing element defines a field of view e.g. a cone shaped viewing field, allowing the surgeon to visually follow the surgery.

The image capturing element is configured to exchange image data with an external monitor, e.g. wirelessly or by a cabled connection. The external monitor could be a fixed monitor of the operating room.

In use, the image capturing element is positioned inside the patient, and the connector connects the image capturing element to the base which is outside the patient. The manipulator may be integrated in, or at least partly integrated in the connector. The manipulator may particularly be for powered movement meaning that it is moved by the help of electrical power or in similar powered way, e.g. by pressurised air etc. Particularly, the manipulator may comprise one or more wires extending into the connector and arranged to bend the connector by pulling one or more wires. Alternatively, or additionally, the manipulator may comprise one or more rotational or linear joints which are operated by electric motors via a motor controller and arranged to rotate the connector or a part thereof, or to move the connector or a part thereof linearly relative to the base.

The connector may extend outwards from the contact surface or from an interface location surrounded by the contact surface. The angle between the connector and the contact surface may particularly be between 60, 70, 80 and 90 degrees, such as e.g. 75 degrees, i.e. the connector may be 15 degrees from being perpendicular to the contact surface.

The connector may comprise an elongated element defining an axial direction. If the connector is cylindrical, e.g. with a circular cross-section, the axial direction is the direction of the centre axis extending through the centre of the circular cross-sections. The image capturing element may particularly be positioned at a distal end of the elongated element and the base may be positioned at an opposite proximal end of the elongated element.

The connector may include a bendable section, and wires may extend into the connector and be attached to the connector such that pulling one or more wires bends the bendable section. This is discussed further relative to the drawings.

The axial direction may be perpendicular to the contact surface at a point of intersection between the connector and the contact surface, and the field of view may be symmetric relative to the axial direction. In case of the latter, a cone forming the field of view has its centre axis in the axial direction.

At least one of the manipulator and the image capturing element may be configured for wired or wireless communication with an external control unit, and at least one of the manipulator and the image capturing element may be configured for independent powering particularly configured to be powered by a battery, e.g. a battery contained in the base, or configured for wired powering, e.g. from an electrical power outlet in the operating room. When used herein, the term "at least one of the manipulator and the image capturing element . . . ", means one, or the other, or both parts.

In one embodiment, the manipulator is controlled manually via a joystick, or similar human interface allowing manual control over the motors. In one embodiment, the surgical camera comprises a position controller e.g. arranged in communication with the manipulator and the image capturing element. The position controller may be configured to carry out a picture analysing sequence to identify a field of interest in an image from the image capturing element and for controlling the manipulator based on the identified field of interest.

In one embodiment, the manipulator, connector, and image capturing element is formed as one component which is releasably attached to the base. By releasing the component from the base, the image capturing element can be manipulated by hand while the base remains attached to the surface of the patient, and the component can be reconnected to the base later, if hands free manipulation of the image capturing element is needed.

The position controller may comprise a communication interface configured to receive data defining a field of interest to be identified in the image. Such data may e.g. define a reference image, e.g. an image of a tip of a forceps or other instruments for minimally invasive surgery. The data may also define a specific colour, or a specific shape of an element attached to the instrument for minimally invasive surgery and thereby allow the position controller to place the field of interest at the element of interest. This feature allows the surgeon to use the instrument while the surgical camera automatically adjusts the position of the image capturing element and thereby automatically provides a suitable field of view.

In one embodiment the position controller may comprise a voice control module capable of receiving voice commands and converting them to motion commands for the manipulator.

In one embodiment the position controller may comprise an eye-tracker control module capable of receiving eye position commands based on viewing of a monitor and converting the eye position commands to motion commands for the manipulator. This will allow the surgeon or an assistant to move the image capturing element by watching a monitor which displays the image form the image capturing element.

The manipulator may comprise at least one rotational joint. One of the at least one rotational joints may rotate the connector about an axis extending parallel to the axial direction. Particularly, rotation about this axis may be caused by rotation of said inner assembly. Alternatively, the joint may be located between the base and the connector to thereby allow rotation of a part of the connector and the image capturing element relative to another part of the connector and the base.

The connector may be deformably bend by wires threaded into the connector. Alternatively, or additionally, the manipulator may include at least one rotational joint providing rotation about a rotation axis perpendicular to the axial direction. This joint may particularly be located between the connector and the image capturing element or between a first connector part of the connector and a second connector part of the connector.

The manipulator may be housed in a housing, and the base may be connected to the housing such that the contact surface is between the housing and the image capturing element. The connector extends from the housing through a passage in the base when the base is attached to the skin surface and the image capturing element and connector is inside the patient. In addition to the manipulator, the housing may contain different electronic components of the surgical camera, e.g. a battery, an antenna and/or various electronic components for wireless communication etc.

Particularly, the electronic components may comprise a light source in light transmitting communication with a light emitter at the image capturing element and/or the electronic components may form the aforementioned position controller capable of controlling the position of the image capturing element relative to the base.

In a second aspect, the disclosure provides an assembly comprising a surgical camera of the kind described above, and a surgical tool configured for use in minimally invasive surgery, wherein the surgical camera comprises a position controller in communication with the manipulator and the image capturing element.

The position controller is configured to carry out a picture analysing sequence to identify an identifier in an image from the image capturing element and for controlling the manipulator based on the identifier.

The surgical tool comprises the identifier attached to or forming a part of the surgical tool.

As an example, the surgical tool may be a forceps with jaws movable relative to each other, and the position controller of the surgical camera may be configured to identify the jaws, and to control the manipulator to position the image capturing element such that the jaws are in the field of view.

In a third aspect, the disclosure provides a method of subjecting a patient to minimally invasive surgery, the method comprising:

providing at least a first patient opening and a second patient opening;

providing a surgical camera or an assembly according to the first or second aspect of the invention;

inserting the connector and image capturing element through the first patient opening;

attaching the contact surface to an outer skin surface of the patient;

establishing image data communication between the image capturing element and an external monitor;

inserting a surgical tool through the second patient opening; and carrying out minimally invasive surgery by use of the surgical tool while monitoring the procedure by use of the surgical camera.

The image data communication may particularly be established prior to the insertion of the surgical tool through the second patient opening.

The method may particularly include the step of insufflating a body cavity in which the image capturing element is inserted. The method may e.g. comprise inserting the image capturing element into the peritoneal cavity, and it may comprise the step of forming the patient opening by use of an obturator which forms part of, or slides in a guide formed by the surgical camera.

The assembly according to the second aspect and the method according to the third aspect may include any of the features or use of any of the features mentioned relative to the surgical camera of the first aspect of the invention.

LIST OF DRAWINGS

The disclosure will now be described in further detail with reference to the accompanying drawings in which.

DESCRIPTION OF EMBODIMENTS

Figure 1:
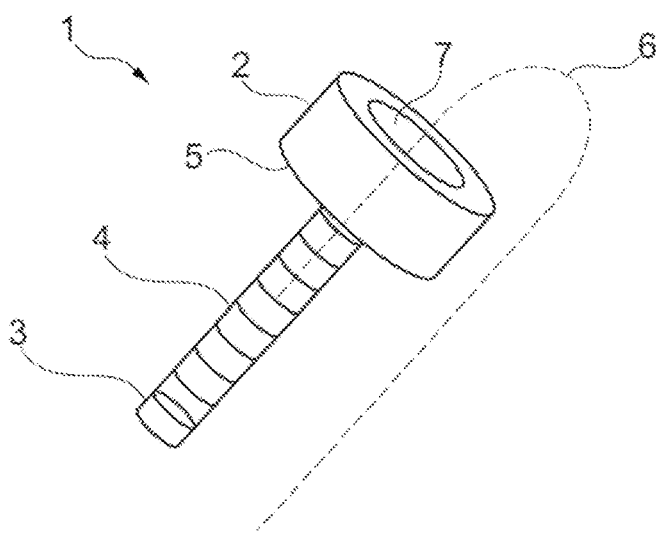
FIG. 1 illustrates a surgical camera.

FIG. 1 illustrates a surgical camera 1 comprising a base 2, an image capturing element 3, and a connector 4 extending between the image capturing element and the base. Additionally, the surgical camera comprises a manipulator which is not visible in FIG. 1. The manipulator is configured with a number of joints or links allowing movement of the image capturing element relative to the base. The manipulator is powered, e.g. by electricity or pressurised air, such that the image capturing element can be moved automatically with no manual interaction.

The base forms a contact surface 5 configured to be attached to an outer skin surface of a patient. The connector extends outwards from the contact surface such that, when attached to the connector at a patient opening, the connector may extend through the patient opening into a connector cavity.

The dotted line 6 illustrates that an a surgical tool, or an obturator may be inserted into an conduit 7.

The connector has an elongated shape which defines the axial direction indicated by the arrow 8.

Figure 2:
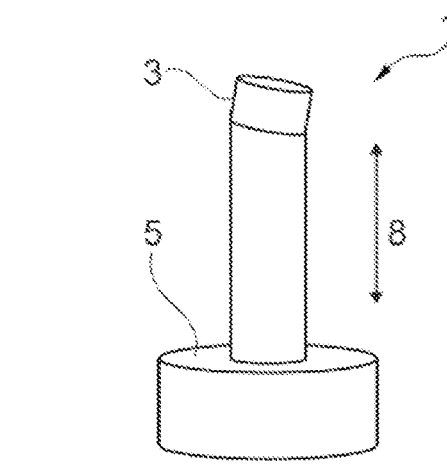
FIG. 2 illustrates a surgical camera from another angle.

FIG. 2 illustrates the surgical camera from another angle and with the image capturing element moved to an angle relative to the axial direction of the connector. In this image, the contact surface 5 can be seen more clearly. The contact surface may comprise an adhesive surface portion e.g. comprising a hydrocolloid adhesive, a double sided adhesive or any kind of known from e.g. a plaster or patch, preferably allowing skin friendly attachment of the surgical camera to the outer skin surface of the patient.

Figure 3:
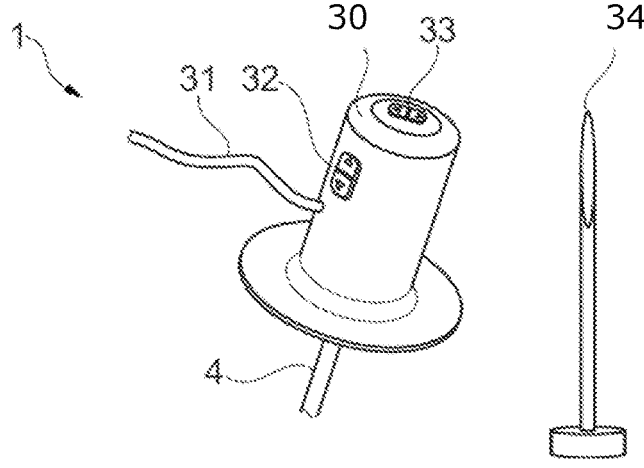
FIG. 3 illustrates a housing formed by the base.

FIG. 3 illustrates a surgical camera with a base and a housing 30 containing at least a part of the manipulator and electronic components of the surgical camera. In this embodiment, the contact surface 5 is located between the housing and the image capturing element 3. A cable connection 31 extends from the base, and operation control buttons 32 are placed on the housing. The cable connection 31 may form communication with electronic components of an external control unit, an external monitor, or simply provide electrical power for operation. The cable connection may e.g. include an HDMI connection.

The electronic components may comprise a light source in light transmitting communication with a light emitter at the image capturing element.

A conduit extends from an opening 33 through the base and connector to an opening at a distal end of the connector, e.g. an opening in the image capturing element. The conduit provides guidance e.g. for a tool 34 which, can be used for surgery.

Figure 4:
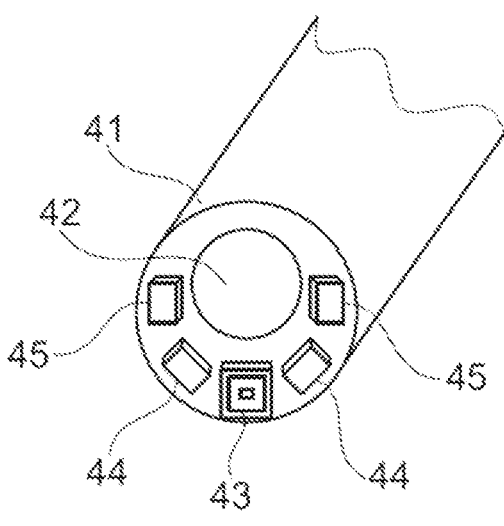
FIG. 4 illustrates an image capturing element of the surgical camera.

FIG. 4 illustrates the distal end 41 of the surgical camera and particularly the image capturing element. In this view, the tool conduit opening 42 in the distal end is clearly seen. The image capturing element comprises a CCD 43, Light emitting diodes 44, and optionally at least one additional CCD or sensor 45 for enabling a 3D picture generation. The CCDs or sensors communicate with a position controller configured to identify a field of interest in an image from the image capturing element. The position controller controls the manipulator based on the identified field of interest.

Figure 5:
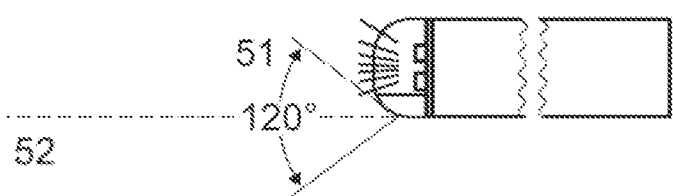
FIG. 5 illustrates details of a field of view.

FIG. 5 illustrates that the field of interest, indicated by the angle 51 is symmetric relative to the axial direction indicated by the arrow 52. The arrow 52 indicates a centre axis of the field of view.

Figure 6:
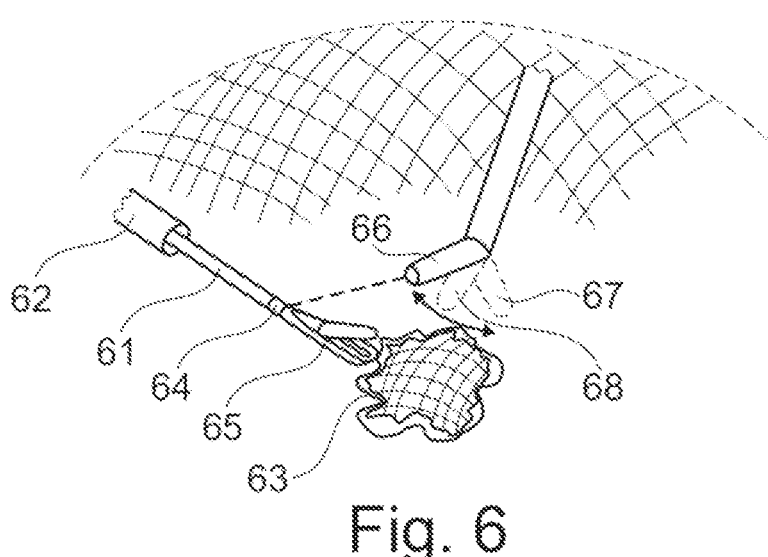
FIG. 6 illustrates the surgical camera inserted into a peritoneal cavity.

FIG. 6 illustrates the surgical camera when inserted in the peritoneal cavity of a patient. A surgical tool 61, in this case surgical forceps, is inserted through the patient opening 62 and manipulates tissue 63 in the peritoneal cavity. The surgical tool comprises an identifier 64 attached above the jaw portion 65. The position controller is programmed to identify this identifier and to operate the manipulator for bringing the identifier into the field of interest. The surgical camera is illustrated with three different positions, 64, 65, 66 of the image capturing element relative to the base.

Figure 7:
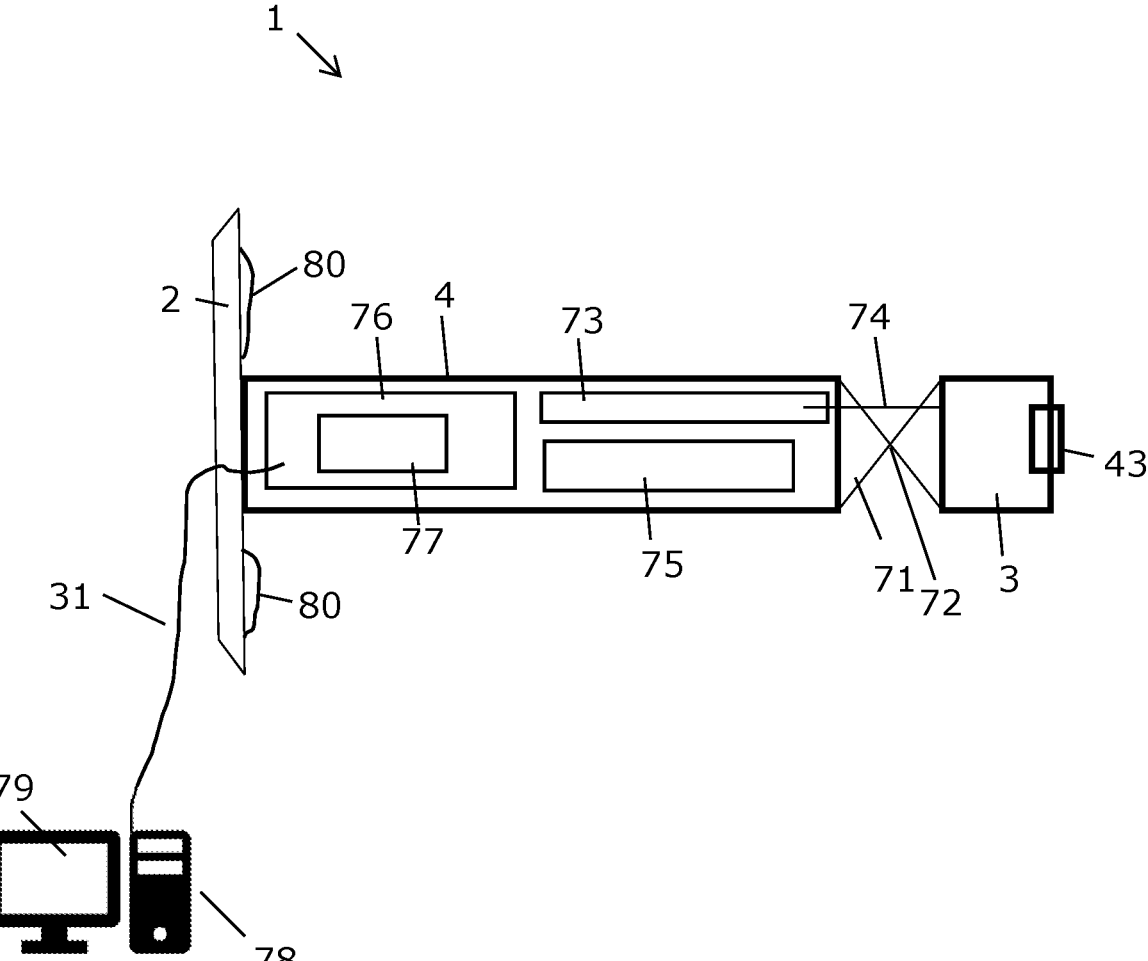
FIG. 7 illustrates schematically a cross section of the surgical camera.

FIG. 7 illustrates schematically a cross section of the surgical camera. The camera comprises a base 2, an image capturing element 3, and a connector 4. The image capturing element 3 comprises a camera structure such as a CCD 43 etc. The image capturing element 3 and the connector 4 are joined in a hinge structure 71 forming a hinge point 72 about which the image capturing element can pivot relative to the connector 4. The manipulator 73 operates via the link 74 which is shifted outwards or rearwards and thereby rotates the image capturing element relative to the connector.

As illustrated in FIG. 7, the manipulator is configured to move the image capturing element relative to the connector. In other embodiments, the manipulator moves the connector relative to the base, and/or moves both the connector relative to the base and moves the image capturing element relative to the connector.

As illustrated in FIG. 7, the manipulator is configured for a relatively simple movement of the image capturing element relative to the connector, namely by rotation about the hinge point 72. The skilled person would readily expect manipulators having more advanced structures for movement in one or more different directions.

The surgical camera comprises a battery 75 providing independent powering of the surgical device, and electronic components 76 including a processor in the form of a CPU 77. The electronic components may communicate with or be replaced with electronic components in an external controller 78. In the illustrated embodiment, the internal electronic components communicate with the external controller via a cable 31. The communication may, alternatively, be wireless.

FIG. 7 illustrates the manipulator being fully integrated or encapsulated in the connector. As indicated in the previous embodiments, the manipulator or parts thereof may also be housed in a housing which is outside the patient, and the connector may extend from the housing into the patient.

In the illustrated embodiment, the base is a thin plaster of a soft pliable material which may follow the shape of the outer skin surface of the patient. As illustrated e.g. in FIG. 3, the base may, alternatively, form a housing for parts of the manipulator and/or electronic components, or the base may be attached to a housing for the electronic components. Particularly, it may be detachably attachable to such a housing.

The processor may execute instructions stored e.g. on a non-transitory computer readable medium to receive the data from the CCD 43 or similar camera unit, and to determine movement of the manipulator to bring a desired object within the field of view. Further, the processor may operate as a motor controller for the motor 73. The motor 73 may be a simple solenoid capable of obtaining a few different positions, or the motor could be a rotational motor, e.g. a servo motor including servo control possibilities.

The processor may operate with exchangeable data, e.g. defining the field of interest, e.g. a specific object of interest such that the object of interest can be changed.

In one embodiment, a therapeutic portion of the body, e.g. a cyst in a uterus may be defined as an object of interest and thereby define the field of interest. In other embodiments, a specific object, e.g. an object on a medical instrument is defined as the object of interest and thereby defines the field of interest.

In the illustrated embodiment, the monitor 79 forms an external graphical user interface. In other embodiments, such a monitor and/or user interface is embedded directly on the base or a housing attached to the base.

The adhesive layer 80 in an inner surface of the base 2 is made from a skin friendly material such as hydrocolloid and facilitates easy and sealing attachment of the surgical camera to an outer skin surface of the patient.

FIGS. 8-14 illustrate further details of an embodiment of the surgical camera.

Figure 12:
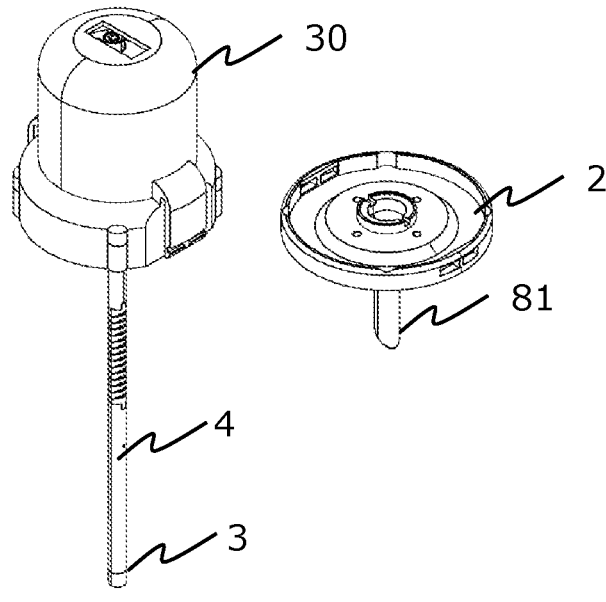

The camera comprises a base 2, an image capturing element 3, a connector 4, and a manipulator which will be described further relative to FIGS. 12 and 14. The base 2, comprises an insertion tube 81 extending outwards from the contact surface 5 and forming a connector passage for receiving the connector 4 through the insertion tube. The insertion tube forms an inclined tip 82 for easy insertion through a body opening.

The insertion tube may also form a passage for an obturator which can be used for piercing the skin of the patient. With the obturator in place, the surgeon can make the patient opening while inserting the insertion tube into the patient. Once in place, the obturator may be pulled out of the connector passage while an internal valve structure seals the connector passage and allows insufflation of the patient cavity into which the image capturing element is inserted. Finally, the connector and image capturing element can be inserted into the connector passage.

Figure 8:
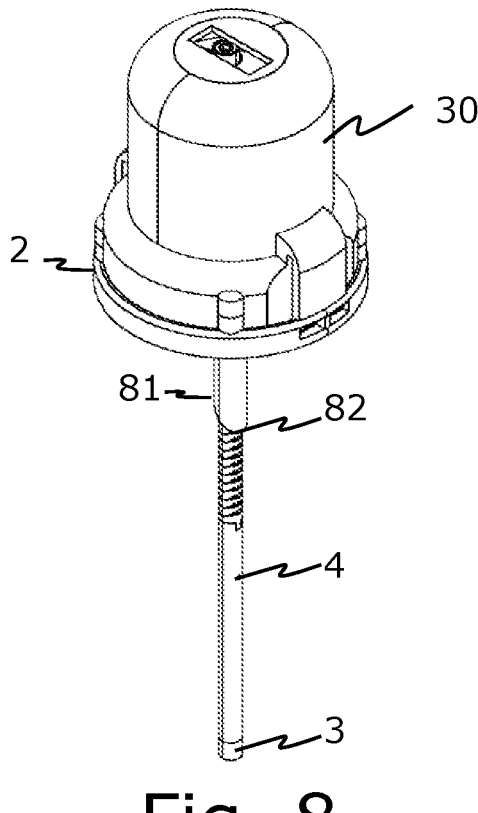
FIGS. 8-14 illustrate details of an embodiment of the camera.
Figure 9:
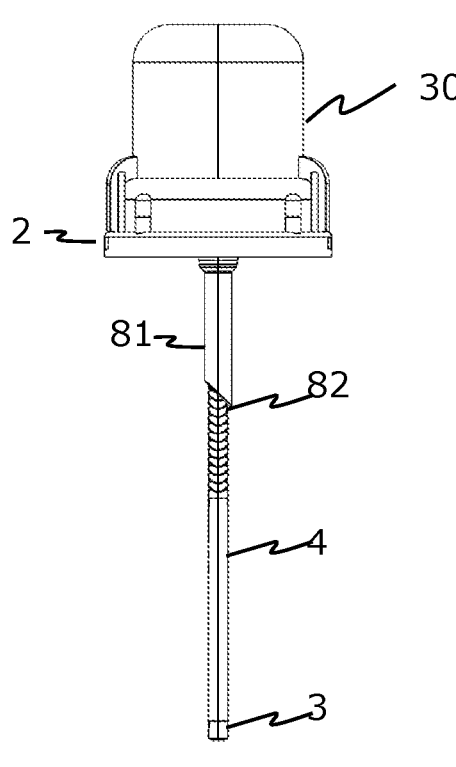
Figure 10:
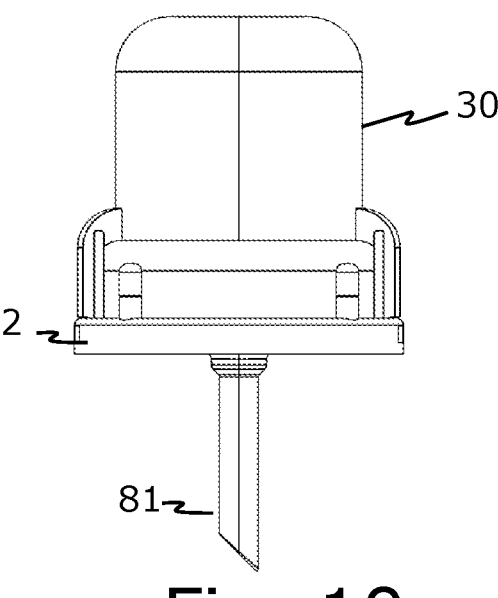
Figure 11:
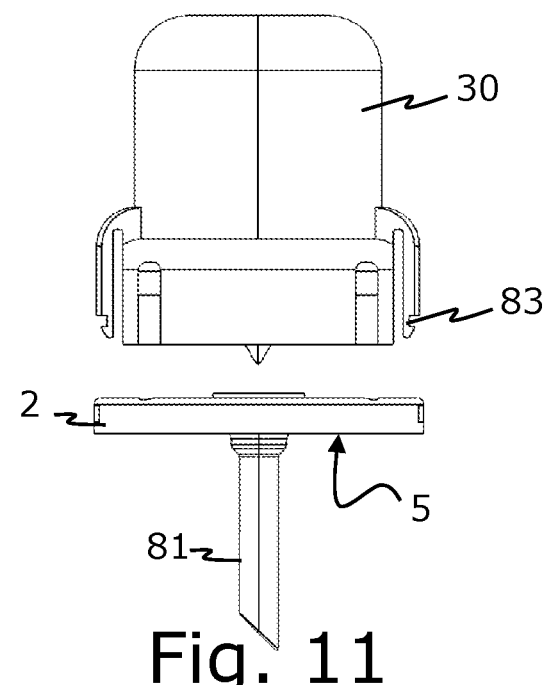

FIGS. 8 and 9 illustrate the camera in a perspective view and a side view, and FIGS. 10-11 illustrate an enlarged view of the base 2. The manipulator and a distal end of the connector are encapsulated in a housing 30 which is attached to the base 2. The proximal end of the connector extends from a lower surface of the housing and through the insertion tube 81 of the base.

In a normal, operational condition, the housing and the base are joined by mechanically interlocking hook structures 83. When the housing is detached from the base, it becomes movable relative to the base and thereby facilitate manual operation of the camera by manipulation of the housing 30 by hand. In an alternative embodiment, the housing and the base are formed not to be detached, e.g. formed in one part.

FIG. 11 illustrates the housing being lifted off from the base. The insertion tube 81 is a part of the base, and the contact surface 5 is a surface of the base. The connector is not shown in FIGS. 10 and 11. In a final assembly, it is rotationally suspended inside the housing and extends downwards from the housing through the connector passage in the base as illustrated in FIGS. 8 and 9. FIG. 12 illustrates the housing with the connector and the base as two separate parts.

Figure 13:
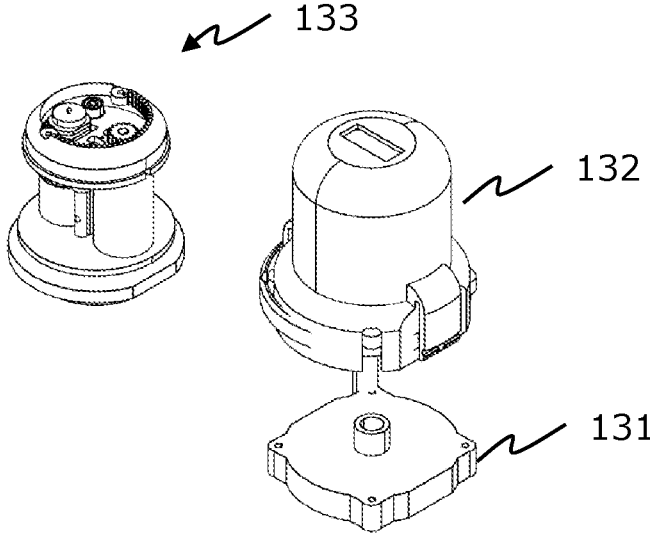

FIG. 13 illustrates main components of the housing 30. The housing comprises a chassis plate 131 and a removable cover shell 132. The chassis plate and the removable shell defines a fixed outer encapsulation for an inner assembly 133, and the inner assembly forms at least a part of the manipulator.

Figure 14:
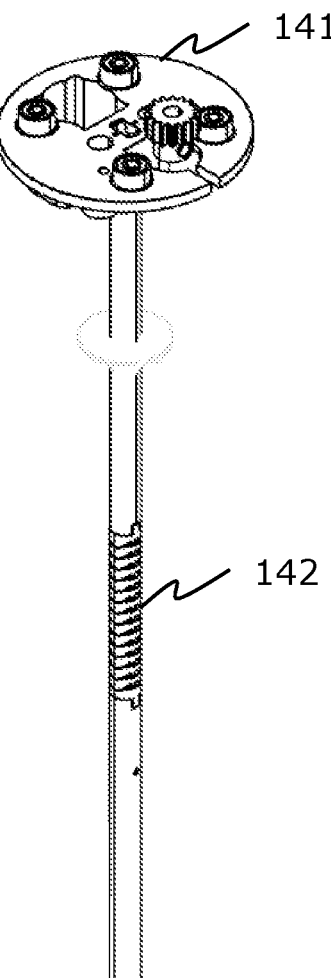

FIG. 14 illustrates details of the connector 4. The connector comprises a connector base 141 arranged inside the housing and configured for cooperation with the inner assembly. The inner assembly defines the manipulator which can rotate the connector and bend the connector and thereby move the image capturing element. The connector may be bended in a manner known per se, e.g. by having a section of the connector being bendable, and by leading wires from a distal end of the connector, passed the bendable section and fixing the wires at a point being proximal to the bendable section. The bendable section can be bended by manipulation of the wire(s). Two wires may be attached at opposite sides of a centre axis through the connector. Bending may be caused by pulling a first one of the wires and releasing the other, second, wire and bending in an opposite direction may be caused by pulling the second wire while releasing the first wire.

Figure 15:
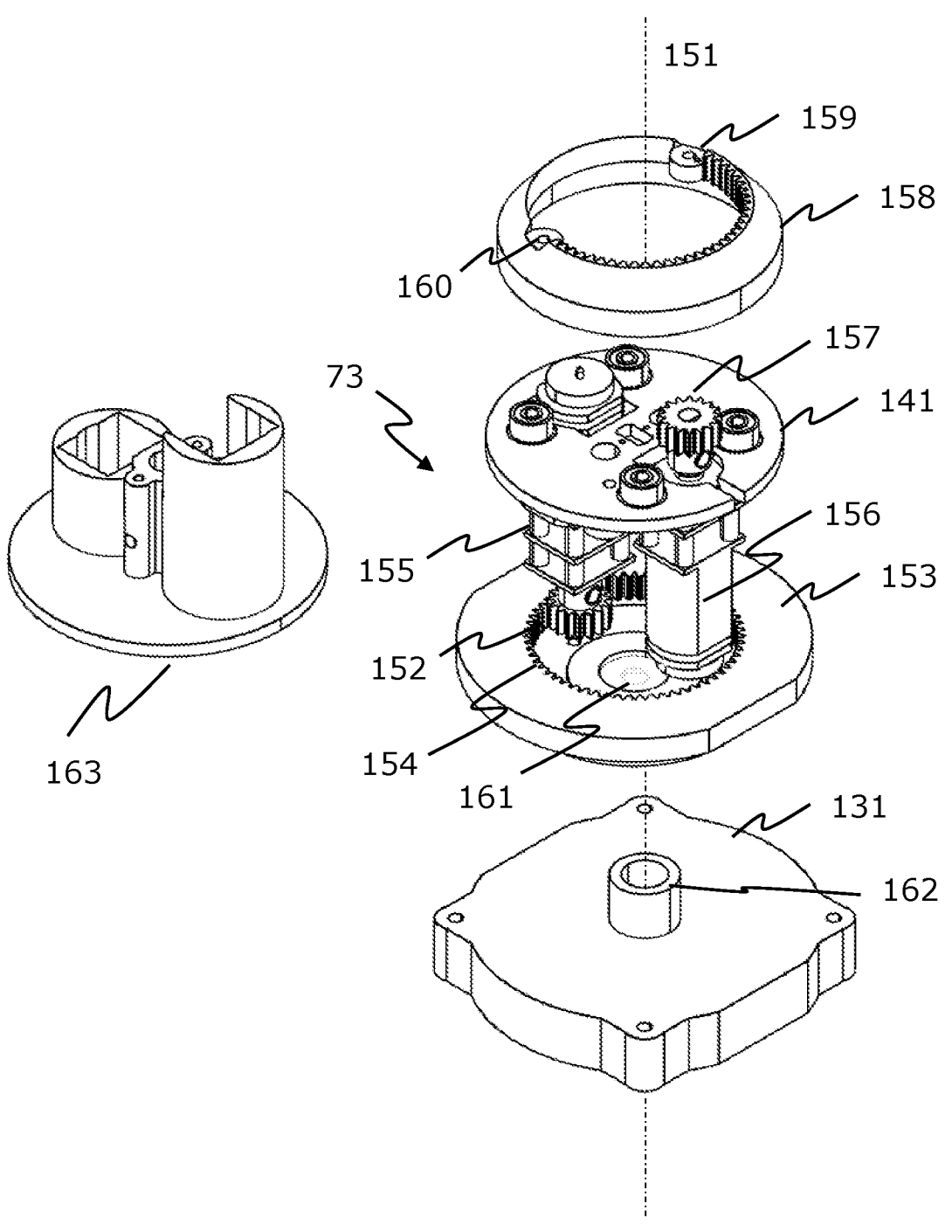
FIG. 15 illustrates an exploded view of an inner assembly

FIG. 15 illustrates details of the inner assembly 133 which defines at least a part of the manipulator 73 and particularly can rotate the connector and manipulate the wires mentioned above.

The inner assembly is rotatable around a central axis illustrated by the dotted line 151 relative to the housing. To facilitate rotation of the inner assembly, it includes a rotational joint with a tooth wheel 152 engaging a tooth ring 153 with internal toothing 154. The tooth ring 153 is fixed to, or forms part of the housing, or more specifically the chassis plate 131 of the housing. When the electric motor 155 which is part of the inner assembly, is activated, it rotates the tooth wheel 152 and thereby rotates the inner assembly relative to the housing.

The inner assembly comprises a second electric motor 156 operating a second tooth wheel 157. The Second tooth wheel rotates a tilt-actuating rotor-ring 158 by engagement with an inner tooting 164 of the tilt-actuating rotor-ring 158. The tilt-actuating rotor-ring rotates relative to the inner assembly.

A tilt actuating wire structure extends from the tilt actuating rotor ring and into the connector 4. The wires extend from the fixation points 159, 160 of the tilt-actuating rotor-ring 158.

The wires are arranged for movement of the image capturing element relative to the base by bending the connector 4. This bending is caused by pulling the wires inside the connector and is caused by a bendable portion of the connector. The bendable portion of the connector is indicated by 142 in FIG. 14.

The connector base 141 is illustrated in FIG. 15, but the connector is left out of FIG. 15. The connector extends from the connector base through the hole 161 in the tooth ring 153 and through the hole 162 in the chassis plate 131.

The motor fixture 163 illustrated as a separate component taken out of the inner assembly. In an assembled state, the motor fixture holds both electric motors in place such that the motors have rotor axes on opposite sides of and with the same distance to the central axis 151.

The motors are identical motors but arranged with the rotor axes in opposite directions with respect to the central axis such that the first motor 155 engages the tooth ring 153 near the interface with the base 2 and the second motor 156 engages the tilt-actuating rotor-ring 158 in an axially opposite end of the housing.

Figure 16:
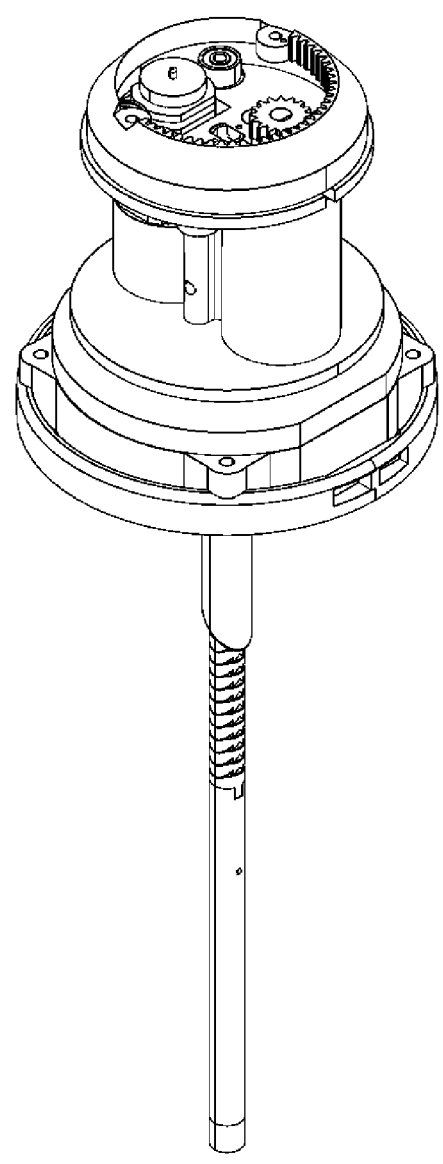
FIG. 16 illustrates the inner assembly and the connector extending from the inner assembly.

FIG. 16 illustrates the inner assembly including the motor fixture 163.

Figure 17:
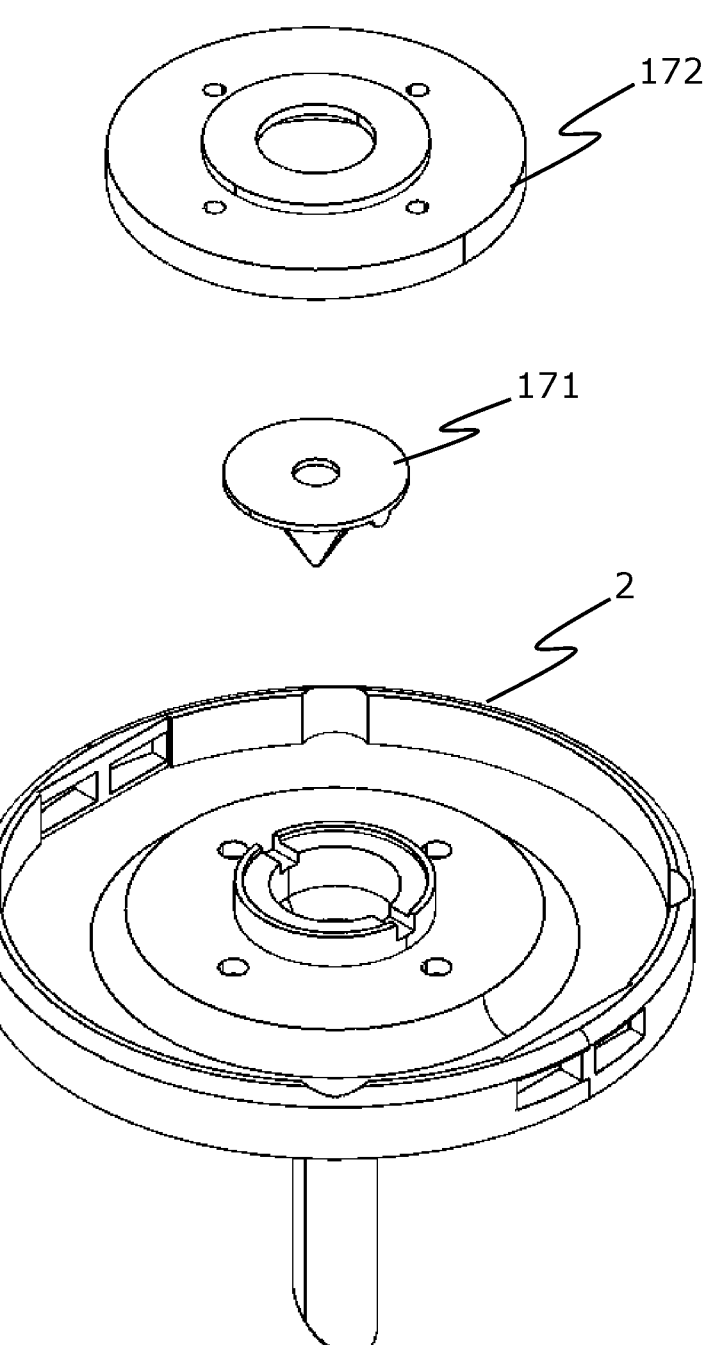
FIG. 17 illustrates an exploded view of the base including a duckbill valve.

FIG. 17 illustrates an exploded view of the base 2 showing a duckbill valve 171 in the connector passage formed by the insertion tube 81 and locked in place by a washer 172. The duckbill valve enables a procedure in which an obturator is inserted in the connector passage. The connector passage thereby forms the obturator conduit, and the base with the obturator can be used for piercing the skin to make the patient opening.

Subsequently, the base is fixed to the skin surface of the patient and the obturator is removed. At this point, the duckbill valve prevents leakage of fluids and air from the body until the connector is inserted through the connector passage. FIG. 17 also illustrates the mechanical fixture for receiving the hook structure 83 of the housing for detachable attachment of the housing and connector to the base.

Figures 18, 19, 20:
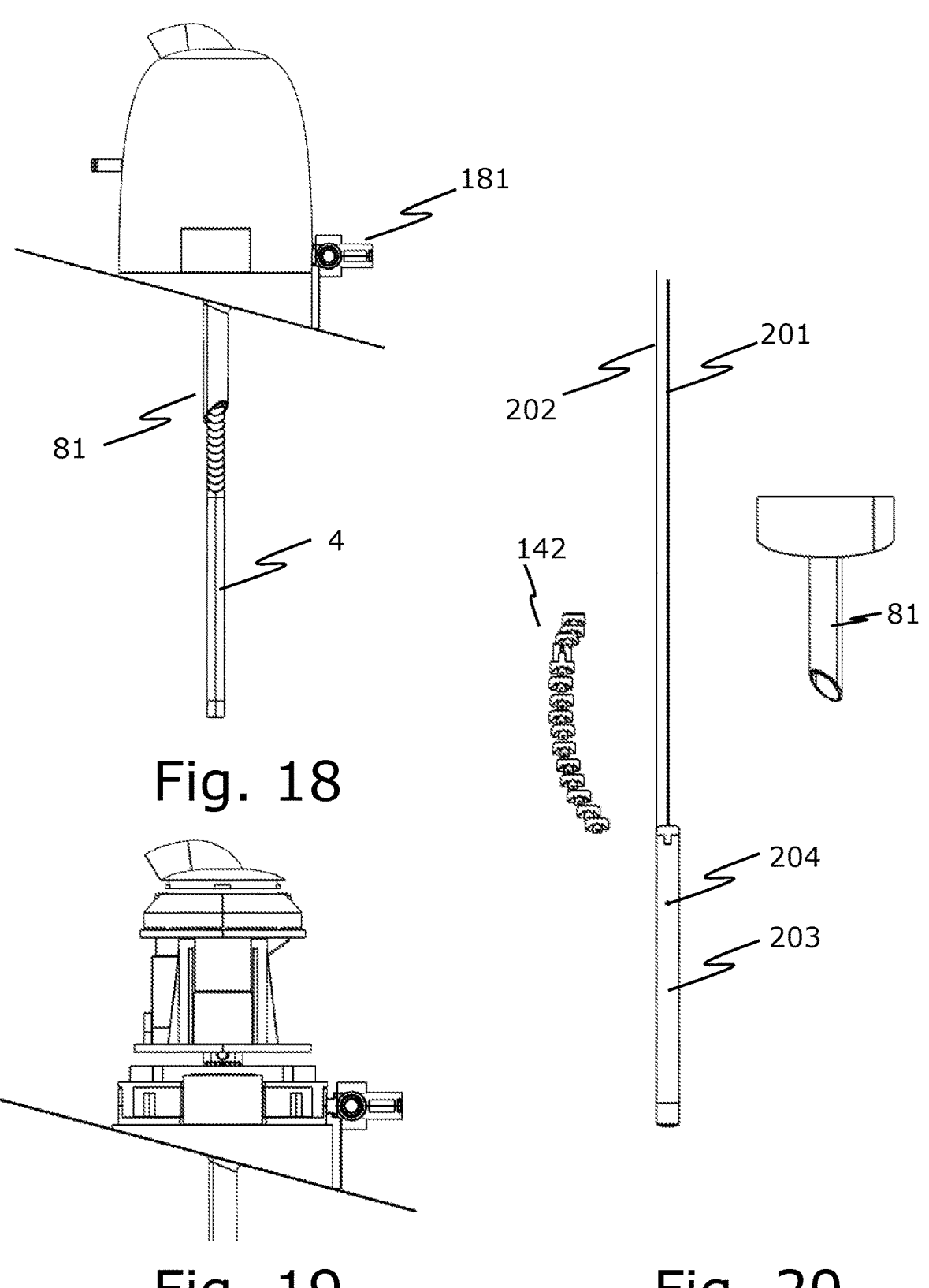
FIGS. 18-19 illustrate an embodiment where the contact surface is inclined and defines an angle different from 90 degrees to the axial direction of the connector.
FIG. 20 illustrates details related to bending of the connector.

FIG. 18 illustrates a sideview of an embodiment where the contact surface 5 is inclined relative to a perpendicular angle to the connector 4, e.g. to an angle of 15 degrees relative to perpendicular, i.e. corresponding to 75 degrees between the contact surface and the connector. For insertion into the peritoneal cavity, angles between 10 and 30 degrees such as 15, 20, or 25 degrees relative to a perpendicular layout may be desired.

The disclosed embodiment comprises a purge structure with an inlet 181. A $CO_2$ source may be attached to the inlet and an internal passage leads to the space between the insertion tube 81 and the connector 4 and thereby allows $CO_2$, or other gases to be inflated into the body, e.g. for expanding the peritoneal cavity etc.

FIG. 19 illustrates the sideview without the cover shell.

FIG. 20 illustrates details of the threading of wires into the connector. The connector comprises a bendable portion which is moved to the links for illustrative purpose. Two wires 201, 202 extend from opposite sides of the tilt-actuating rotor-ring 158 into the connector where they are attached at opposite sides of the wall of the lower connector section 203 at the fixation point 204. When one wire is pulled and the other wire is released, the bendable portion 142 bends.

The invention claimed is:

1. A surgical camera comprising:
a base;
an image capturing element defining a field of view and configured to exchange image data with a monitor;
a connector extending between the image capturing element and the base; and
a manipulator configured for movement of the image capturing element relative to the base,
wherein the manipulator is at least partly encapsulated in a housing detachably attachable to the base,
wherein the connector forms part of an inner assembly located in the housing and rotatable around a central axis relative to the housing via a first rotational joint,
wherein the base forms a contact surface configured to be attached to an outer skin surface of a patient, and
wherein the base comprises:
an insertion tube extending outwards from the contact surface and forming a connector passage for receiving the connector through the insertion tube; and
a duckbill valve arrange to seal the connector passage in the insertion tube, the duckbill valve being located in level with the first rotational joint.

2. The surgical camera according to claim 1, wherein the manipulator comprises a tilt-actuating rotor-ring and a tilt actuating wire structure with at least one wire extending from a fixation point in the connector to a point on the tilt actuating rotor-ring, wherein the at least one wire is arranged for movement of the image capturing element relative to the base by pulling, and the tilt-actuating rotor-ring is rotatable relative to the inner assembly by a second rotational joint to thereby cause the pulling.

3. The surgical camera according to claim 2, wherein the at least one wire is arranged for movement of the image capturing element relative to the base by bending of a bendable portion of the connector.

4. The surgical camera according to claim 2, wherein the tilt-actuating rotor-ring is rotatable around the central axis.

5. The surgical camera according to claim 1, wherein the housing comprises a chassis plate and a removable cover shell, and wherein a first inner toothing is provided on the cover shell to allow manual operation by rotation of the housing relative to the base.

6. The surgical camera according to claim 1, comprising a position controller in communication with the manipulator and the image capturing element, the position controller being configured to carry out a picture analysing sequence to identify a field of interest in an image from the image capturing element and for controlling the manipulator based on the identified field of interest.

7. The surgical camera according to claim 6, wherein the position controller comprises a communication interface configured to receive data defining a field of interest to be identified in the image.

8. A surgical camera comprising:
a base;
an image capturing element defining a field of view and configured to exchange image data with a monitor;
a connector extending between the image capturing element and the base;
a manipulator configured for movement of the image capturing element relative to the base; and
a first motor arranged for rotation of an inner assembly relative to a housing and a second motor arranged for rotation of a tilt actuating rotor-ring relative to the inner assembly,
wherein the manipulator is at least partly encapsulated in the housing detachably attachable to the base,
wherein the connector forms part of the inner assembly located in the housing and rotatable around a central axis relative to the housing via a first rotational joint; and
wherein the first motor and the second motor each has a rotor axis, and the rotor axes are arranged with the same distance to the central axis.

9. The surgical camera according to claim 8, wherein the rotor axes are arranged on opposite sides of the central axis.

10. The surgical camera according to claim 8, wherein the first motor engages a first inner toothing of a fixed outer shell by a first tooth wheel, the second motor engages a second inner toothing of the tilt actuating rotor-ring by a second tooth wheel, and the first and second tooth wheels are offset in the direction of the central axis.

11. The surgical camera according to claim 8, wherein the first and second motor are identical motors but arranged with the rotor axes in opposite directions with respect to the central axis.

12. An assembly comprising:
a surgical camera according to claim 1; and
a surgical tool configured for use in minimally invasive surgery,
wherein the surgical camera comprises a position controller in communication with the manipulator and the image capturing element, the position controller being configured to carry out a picture analysing sequence to identify an identifier in an image from the image capturing element and for controlling the manipulator based on the identifier.

13. A method of subjecting a patient to minimally invasive surgery, the method comprising:

providing at least a first patient opening and a second patient opening;

providing a surgical camera according to claim 1;

inserting the connector and image capturing element through the first patient opening;

attaching a contact surface to an outer skin surface of the patient;

establishing image data communication between the image capturing element and an external monitor;

inserting a surgical tool through the second patient opening; and carrying out minimally invasive surgery by use of the surgical tool while monitoring the procedure by use of the surgical camera.

14

14. The method according to claim 13, wherein the image data communication is established prior to the insertion of the surgical tool through the second patient opening.

15. The method according to claim 13, wherein the image capturing element is inserted into a cavity of the patient, and the cavity is insufflated until a free space is established around the image capturing element.

16. The method according to claim 13, wherein the image capturing element is inserted into a cavity of the patient, and the cavity is sealed by adhesively attaching the base to the outer skin surface of the patient.

17. The method according to claim 13, wherein the image capturing element is moved relative to the base by detaching the housing from the base and moving the image capturing element by moving the housing relative to the base.

\* \* \* \* \*